United States Patent [19]

Tzeng

[11] 4,205,445
[45] Jun. 3, 1980

[54] DENTAL SURVEYOR

[75] Inventor: Chieh-Fu Tzeng, Downers Grove, Ill.

[73] Assignee: Howmedica, Inc., New York, N.Y.

[21] Appl. No.: 927,430

[22] Filed: Jul. 24, 1978

[51] Int. Cl.² .............................................. A61C 3/00
[52] U.S. Cl. ........................................ 433/50; 433/51
[58] Field of Search ................... 488/35; 32/67, 40 R, 32/32; 33/27 D

[56] References Cited

U.S. PATENT DOCUMENTS

| | | | |
|---|---|---|---|
| 1,482,149 | 1/1924 | Remy | 32/32 |
| 2,095,665 | 10/1937 | Greth | 32/32 |
| 2,108,980 | 2/1938 | Wills | 32/32 |
| 2,189,585 | 2/1940 | King et al. | 33/27 D |
| 2,457,090 | 12/1948 | Ringle et al. | 32/32 |
| 2,616,176 | 11/1952 | Rodin | 32/67 |
| 3,277,576 | 10/1966 | Kraft | 32/40 |
| 3,344,525 | 10/1967 | Harris | 32/69 |
| 3,417,471 | 12/1968 | Mitchell | 32/67 |
| 3,628,252 | 12/1971 | Muller | 33/32 C |
| 4,007,531 | 2/1977 | Anderson | 32/32 |

OTHER PUBLICATIONS

Micro-Analyzer Instruction Manual, Copyright 1956, by Austenal, Inc.

Primary Examiner—Robert Peshock
Attorney, Agent, or Firm—Francis X. Murphy; Charles J. Knuth; Lawrence C. Akers

[57] ABSTRACT

A novel dental surveyor for use in analyzing and working upon dental models is disclosed. The surveyor contains one or more vertical tools, such as marking tools, wax relieving tools and tapered tools. Rotation of a spindle received within a sleeve about its longitudinal axis, combined with horizontal sliding of tool housings upon tool support means attached to said spindle, allows the tools to contact the entire surface of a dental model while always remaining oriented in the vertical direction. The surveyor may also be equipped with e.g. a grinding or drilling tool and means for locking such a tool against horizontal movement while in use.

7 Claims, 4 Drawing Figures

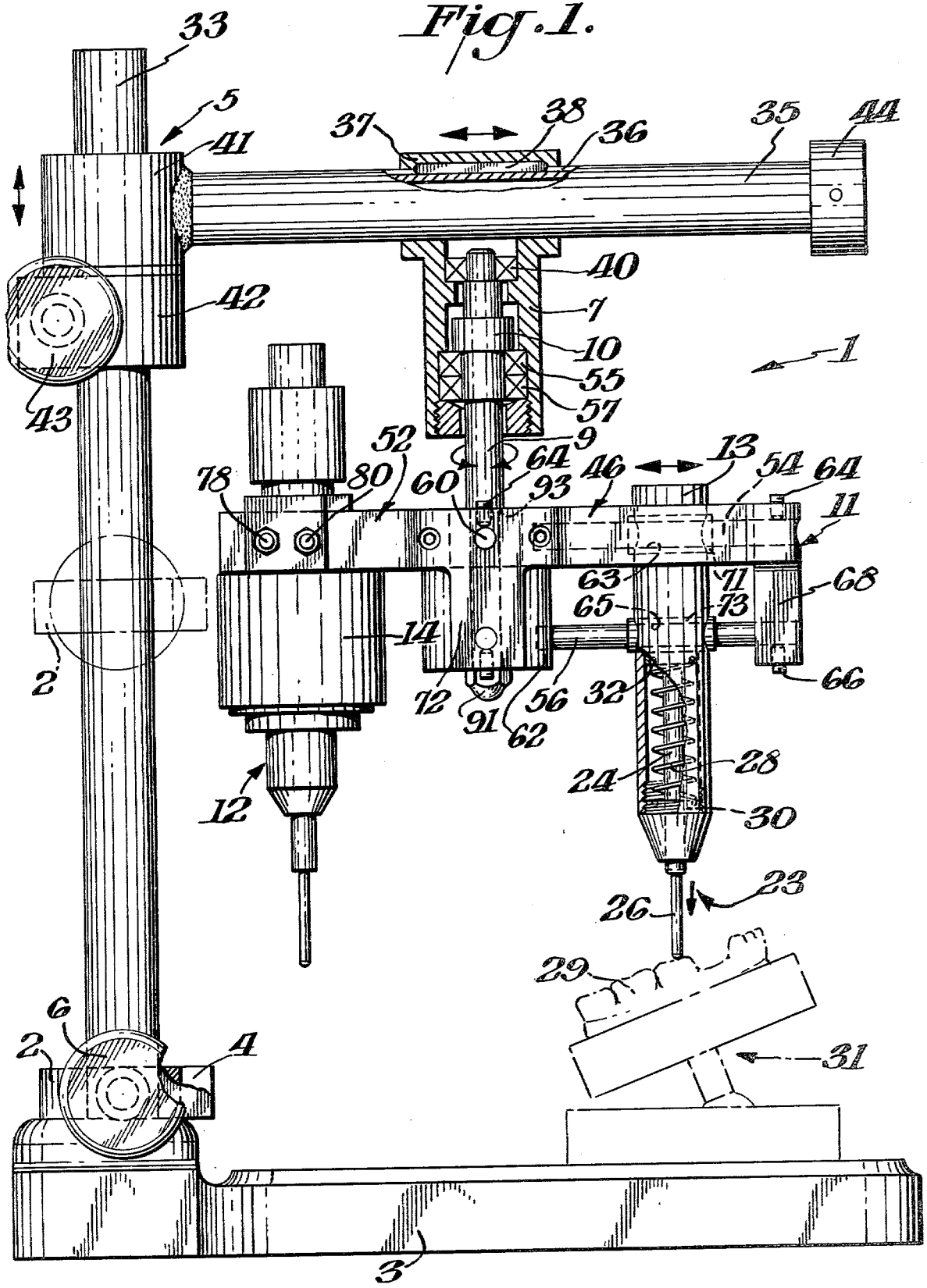

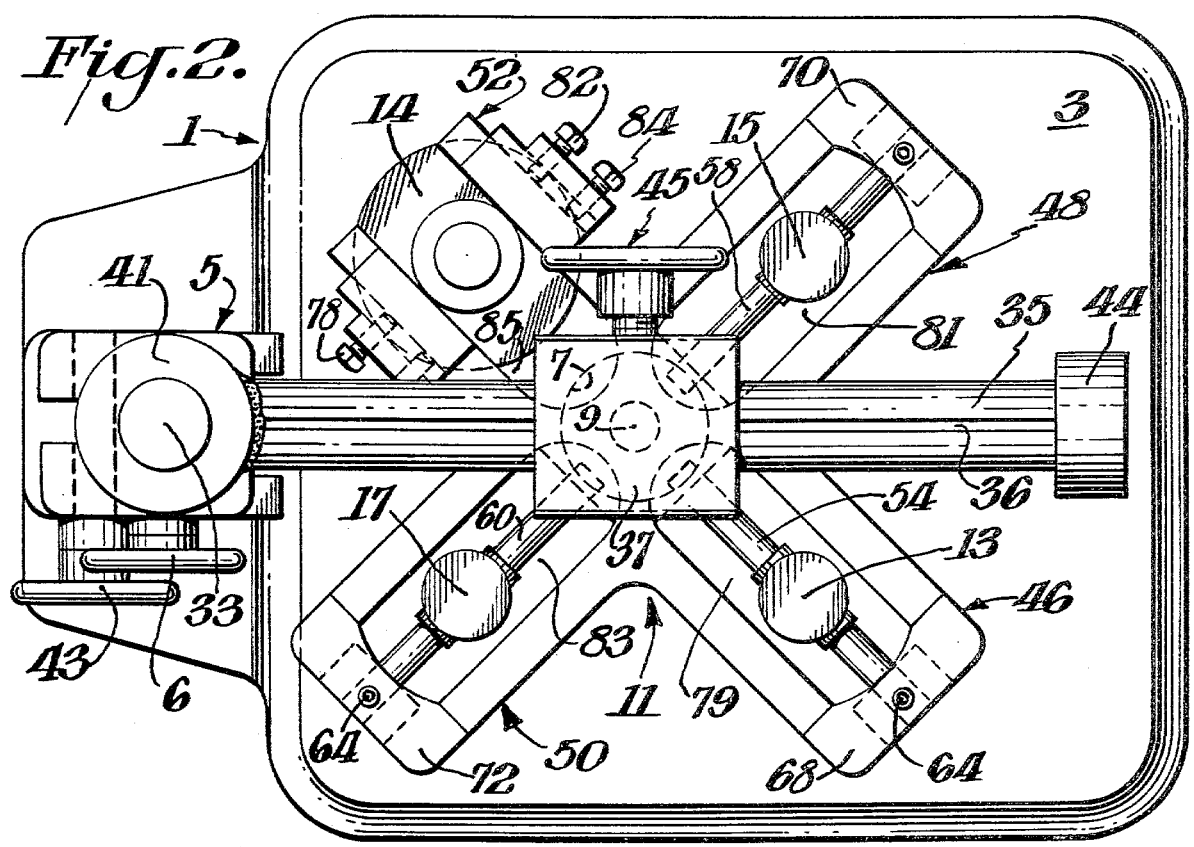
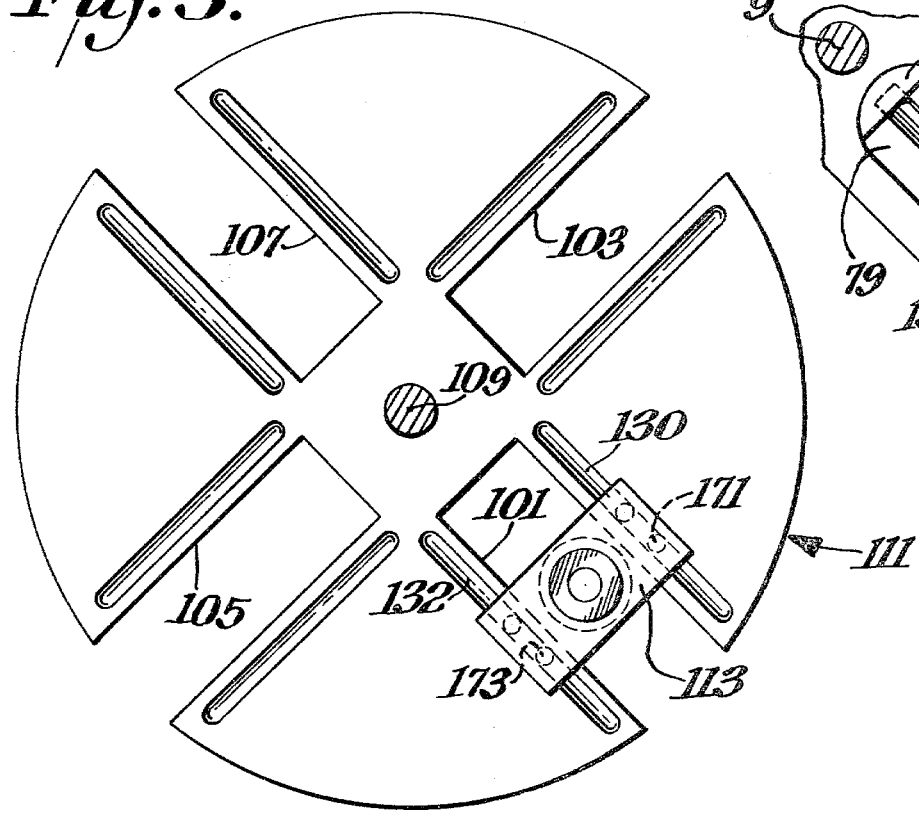
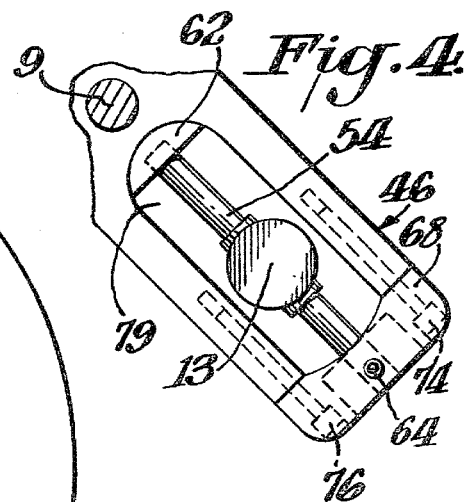

4,205,445

DENTAL SURVEYOR

BACKGROUND OF THE INVENTION

A variety of surveying and paralleling instruments are widely used in the art of preparing dental restorations, such as removable and fixed bridges and dentures, from dental models of the teeth of the recipient. Thus, for example, dental surveyors are used to determine the largest contours of those viable teeth to which a denture will be anchored. Generally, anchoring clasps are placed just below the line of the largest contour. Also, dental surveyors are used for wax relief of undercut areas of abutment teeth and to locate paths of insertion. Paralleling insturmentation is also used in the precision dowel pin technique in the manufacture of dentures and bridgework. Paralleling instrumentation may also be used in a variety of other grinding, milling, drilling and parallel pin work operations. In all of these applications it is highly desirable for accuracy that the tool contacting or operating upon the dental model always remain oriented in the vertical direction as it passes from point to point upon the dental model.

One class of prior art dental surveyor is the hinged arm surveyor. This type of surveyor comprises a vertical support and a horizontal hinged arm extending from the support and holding a surveying tool at its end. Rotation of the horizontal arm about the axis of the vertical support, combined with elbow-like relative rotation of the two components of the horizontal arm, allows for movement of the tool upon the dental mode. However, because the two components of the moving hinged arm must remain in perfect horizontal alignment in order to maintain the vertical alignment of the tool, the hinged arm must be bulky in construction. Thus, this type of instrument tends to respond heavily and somewhat sluggishly to the touch of the operator using it.

Another type of prior art dental paralleling instrument is the Austenal Micro-Analyzer (Howmedica Inc., Dental Division, Chicago, Illinois). This instrument comprises a vertical support, a horizontal cantilever extending therefrom, with the cantilever being rotatable about the axis of the vertical support, and a tool bar which is horizontally slidable within the cantilever. The rotation of the horizontal cantilever about the vertical support, combined with the horizontal sliding of the tool bar within the cantilever, provides for full movement of the vertically oriented tool upon the dental mode. This surveyor is capable of producing highly accurate work and has achieved considerable acceptance in the art. However, because the horizontal cantilever must remain in precise horizontal orientation and also serve as a moving part, a heavy construction is necessary and the response of this type of surveyor to the touch of the operator is not as light as would be desired.

SUMMARY OF THE INVENTION

A novel surveying instrument comprising a base, a support frame mounted upon said base, a vertical sleeve carried by said frame, a spindle rotatably received within said sleeve, tool support means attached to said spindle below said sleeve, at least one tool housing mounted for horizontal sliding upon said tool support means and a vertical tool carried by each of said tool housings has now been invented. The combination of rotation of the spindle about its longitudinal axis and the horizontal sliding movement of the tool housing upon the tool support means attached to said spindle provides for full movement of each tool upon the entire surface of the dental model, while maintaining the desired vertical tool alignment. The vertical height of the tool arbor and bit of each vertical tool may be adjusted with respect to the tool support means by compression spring means.

An important feature of the novel surveyor is that it contains no bulky, heavy moving parts, and thus the operator may grip a tool and move it easily over the entire dental model with little resistance encountered, especially when ball bearing means are included to facilitate rotation of the spindle within the vertical sleeve and ball bushing means are included to facilitate the horizontal sliding of the tool housings upon the tool support means. Preferably, a plurality of tool housings carrying different vertical tools, for example, a marking tool, a wax relief tool, a tapered tool, etc., are mounted for horizontal sliding upon the tool support means. Thus, the operator does not have to expend the time and effort of removing one tool from a single tool carrier and replacing it with another in order to change tools. Furthermore, the surveyor of this invention may also be equipped with one or more tool housings mounted upon, but lockable against horizontal sliding upon, the tool support means, a vertical tool such as a grinding or drilling tool carried by each of said lockable tool housings and means to lock the surveyor so as to prevent rotation of the spindle within the vertical sleeve. Horizontal movement of the vertically aligned e.g. grinding or drilling tool during its use can thus be prevented.

DETAILED DESCRIPTION OF THE INVENTION

The invention will be described in detail with reference to certain preferred embodiments thereof. Reference to these embodiments does not limit the scope of the invention, which is limited only by the scope of the claims.

In the drawings:

FIG. 1 is a side elevation view of a dental surveyor of this invention, with cut out sections showing details within the vertical sleeve and a tool housing, and with two tools not shown;

FIG. 2 is a top plan view of the surveyor of FIG. 1, with the spindle rotated by 45° from its position in FIG. 1;

FIG. 3 is a top plan view of alternative tool support means from that shown in FIGS. 1 and 2; and FIG. 4 is a top plan view of one arm of the tool support means shown in FIGS. 1 and 2.

A dental surveyor of this invention 1 is shown in FIGS. 1 and 2. It comprises a base 3, a support frame 5 mounted upon base 3, a vertical sleeve 7 carried by support frame 5, a spindle 9 rotatably received within vertical sleeve 7, tool support means 11 attached to spindle 9 below vertical sleeve 7, three tool housings 13, 15 and 17 sidably mounted for horizontal translation upon tool support means 11 and three vertically oriented tools, e.g. 23, carried by the respective tool housings. The tools carried by housnigs 15 and 17 are not shown. The surveyor works upon dental mode 29 held by model holder 31, which rests upon base 3.

In the illustrated embodiment support frame 5 comprises a vertical trunk 33 and a horizontal cantilever arm 35 extending from trunk member 33. Sleeve 7 is carried by cantilever arm 35 by means of head 37. The upper outer surface of cantilever arm 35 is provided with a keyway 36 into which fits a key 38 on the upper inner surface of head 37. Alternative means of assuring the necessary vertical alignment of sleeve 7, such as by providing the inner surface of head 37 and the outer surface of arm 35 with complimentary rectangular shapes may also be employed. Gross adjustments of the location of tool support means 11 are made by vertically sliding collar 41 of cantilever arm 35 upon vertical trunk 33 and locking it into place with collar 42, rotating collar 41 about the longitudinal axis of vertical trunk 33, and/or horizontally sliding head 37 upon cantilever arm 35. Said horizontal sliding is limited by stop 44 on arm 35. Collars 41 and 42 are locked at their desired positions against relative rotation about the longitudinal axis of trunk 33 by, e.g., a spring-seated ball locking device. These gross adjustments are locked into place by standard screw means 43 and 45 and are not changed while the surveyor is actually being used to work upon the dental mode. As an alternative, rack and pinion means may be used to raise arm 35 upon trunk 33. Also, the configuration of the base and support frame may, of course, be altered from that shown in the drawings. Generally, any configuration is acceptable which insures that the sleeve will be carried by the support frame so as to maintain constant vertical alignment.

Spindle 9 is received within vertical sleeve 7 and rotates about its vertical longitudinal axis within the sleeve. The ease of rotation of spindle 9 within vertical sleeve 7 is enhanced by the presence of ball bearings 40, 55 and 57. Spindle 9 is restrained from dropping out of vertical sleeve 7 by the impingement of shoulder 10 of spindle 9 against ball bearing 55.

Tool support means 11 is removably attached to spindle 9 below the lower end of vertical sleeve 7, such as with a nut 91 screwed upon the threaded lower end of the spindle so as to retain the tool support means tightly between nut 91 and a shoulder 93 on the surface of the spindle. In the embodiment of FIGS. 1, 2 and 4 the tool support means 11 comprises a tool support frame having four arms 46, 48, 50 and 52, and three pairs of parallel horizontal bars, e.g. 54 and 56, with each of tool housings 13, 15 and 17 horizontally sliding upon one of said pairs of bars. It is to be understood however that a greater or lesser number of pairs of parallel bars, such as only a single pair carrying one tool, may also be employed. Additionally, other designs for the tool support means are possible, such as the slotted disc design shown in FIG. 3. The parallel bar design is generally favored, however, because it can carry a plurality of tools without substantially impairing the breadth of vision of the operator while the surveyor is in use and because it provides an absolute check against tilting of the tools from their vertical alignment. Generally, one of the vertical tools supported by the tool support means will be a marking tool suitable for use in determining largest contours of teeth.

Parallel horizontal bars, e.g. 54 and 56, are held in place within tool support means 11 by inner partial cylindrical pieces, e.g. 62, and end pieces 68, 70 and 72 in the arms 46, 48 and 50. End pieces 68, 70 and 72 are secured to the major portions of arms 46, 48 and 50 by horizontal screws, e.g. 74 and 76. The compressive forces generated by the tightened screws, e.g. 74 and 76, are sufficient to maintain the partial cylindrical inner pieces, e.g. 62, in place. Each pair of parallel horizontal bars, e.g. 54 and 56, is carried by the corresponding inner partial cylindrical, e.g. 62, and end, e.g. 68, pieces as shown in FIGS. 1, 2 and 4. The bars are carried by the inner pieces by compressive forces only, but are positively affixed to end pieces 68, 70 and 72 by standard set screw means, e.g. 64 and 66.

Thus it can be seen that any horizontally slidable vertical tool, e.g. 23, can be easily replaced with a non-slidable vertical tool, e.g. 12, by simply releasing screws 74 and 76, removing pieces 62 and 68 together with bars 54 and 56 and tool housing 13, and then installing the desired non-slidable tool housing. The opposite procedure, wherein a non-slidable tool is replaced with a slidable tool, can of course also be performed. Tool 12 may be, for example, an air driven drilling or grinding tool. Its housing 15 is secured within slot 85 in arm 52 by screws 78, 80, 82 and 84. When using such a tool it is generally desired to prevent horizontal movements of the tool bit. To accomplish this end spindle 9 is rotated 180° from its position in FIG. 1, locking block 2 is raised to the position shown in phantom outline in FIG. 1, with the lower portion of end piece 68 snuggly held by vertical slot 4 is block 2, and block 2 then locked into place on trunk 33 by screw means 6.

Precision dowel pin work may be accomplished with a surveyor of this invention by installing a special chuck (not illustrated) upon an arbor of one of the slidable tools and using appropriate attachments known to those skilled in the art. Rotation of spindle 9 within sleeve 7 is prevented by locking block 2 as described above while performing dowel pin work.

In FIGS. 1, 2 and 4, three tool housings 13, 15 and 17 are mounted upon tool support means 11, with each pair of upper 54, 58 and 60 and lower, e.g. 56, parallel horizontal bars passing through bores, e.g. 63 and 65, in the corresponding tool housing. Each tool housing slides horizontally upon its own pair of bars, e.g. 54 and 56. Thus, the tool housings, and of course the tools themselves, are always maintained in a vertically aligned position. The ease of horizontal sliding is enhanced by ball bushings, e.g. 71 and 73. The upper portions of the cylindrical tool housings pass, as said horizontal sliding takes place, within slots 79, 81 and 83 in arms 46, 48 and 50, with the width of these slots being greater than the diameter of the tool housings. Note that the plane formed by the axes of a pair of said horizontal parallel bars does not necessarily have to be a vertical plane, as is shown in the drawings.

Each of the vertically oriented slidable tools, e.g. 23, comprises a tool arbor 24 and a tool bit 26 held by the arbor by, e.g., known taper hole means. The tool bits directly contact and work upon the dental model 29 and may be readily interchanged without removing the tool arbor from the surveyor. Tool bit 26 can be lowered by pulling arbor 24 against the force of compression spring 28 seated inside housing 13 against flange 30 and head 32 on the upper end of arbor 24. Cessation of pulling by the operator forces the tool bit and arbor to retract upward until the spring 28 loses its compression.

In using the surveyor, the operator will properly orient the dental model within the model holder, make the gross adjustments to the location of the tool suport means discussed earlier and then proceed to work upon the dental model by gripping the appropriate tool and moving it in the desired direction. The tool may be freely moved upon the dental mode, with two-dimensional motion accomplished by a combination of rotation of spindle 9 within vertical sleeve 7 and horizontal sliding of tool housing 13, 15 and 17 upon tool support means 11. The tool remains oriented in a vertical direction as it is moved. Fine adjustments to the vertical displacements of the tool bits, e.g. 26, with respect to the vertical location of the tool support means 11, may be made by pulling or relaxing the compression spring means described above. One highly advantageous feature of the dental surveyor of FIGS. 1, 2, and 4 is that is possesses no heavy parts such as hinged arms that must both insure vertical alignment of a tool and at the same time move so as to allow the tool to cover a two-dimensional area. Thus, the dental technician or operator experiences little resistance to motion as he used the tool and can work more accurately and efficiently because of the light touch and feel of the dental surveyor.

An alternate tool support means 111 is shown in FIG. 3. Tool support means 111 is a slotted disc with four tool housings, e.g. 113, horizontally sliding along slots 101, 103, 105 and 107. Preferably, the slots are straight and oriented radially with respect to the axis of rotation of spindle 109, resembling in this way the parallel bar arrangement. The vertical tool alignment is maintained by providing grooves such as 130 and 132 in the disc which serve as tracks for balls, e.g. 171 and 173. These balls also serve to enhance the ease of horizontal sliding of the tool housings upon the slotted disc 111. Compression spring means are again used to allow a fine vertical adjustment of the displacement of the tool bits with respect to the tool support means (i.e. the slotted disc) 111. The surveyor containing the tool support means of FIG. 3 is operated in the same manner as is the surveyor of FIGS. 1, 2 and 4.

What is claimed is:

1. A dental surveyor comprising
   (a) a base;
   (b) a support frame mounted upon said base;
   (c) a vertical sleeve carried by said frame;
   (d) a spindle rotatably received within said sleeve;
   (e) tool support means attached to said spindle below said sleeve, said tool support means including a pair of parallel horizontal bars;
   (f) a tool housing mounted upon said pair of parallel bars for horizontal sliding along a straight path radial with respect to the axis of rotation of said spindle; and
   (g) a vertical tool carried by said tool housing.

2. A surveyor of claim 1 wherein said surveyor comprises a plurality of tool housings, each of said tool housings carrying a vertical tool, and said tool support means includes a plurality of pairs of parallel horizontal bars, with each of said tool housings being mounted upon one of said pairs of parallel bars for horizontal sliding along a straight path radial with respect to the axis of rotation of said spindle.

3. A dental surveyor comprising
   (a) a base;
   (b) a support frame mounted upon said base;
   (c) a vertical sleeve carried by said frame;
   (d) a spindle rotatably received within said sleeve;
   (e) tool support means attached to said spindle below said sleeve;
   (f) a tool housing mounted for horizontal sliding upon said tool support means;
   (g) a vertical tool carried by said tool housing;
   (h) ball bearing means to facilitate the rotation of said spindle within said sleeve; and
   (i) ball bushing means to facilitate the horizontal sliding of said tool housing upon said tool support means.

4. A dental surveyor of claim 3 wherein said surveyor comprises a plurality of tool housings mounted for horizontal sliding upon said tool support means and ball bushing means to facilitate the horizontal sliding of said tool housings upon said tool support means, with each of said tool housings carrying a vertical tool.

5. A dental surveyor of claim 4 wherein each of said tool housings slides upon said tool support means along a straight path radial with respect to the axis of rotation of said spindle.

6. A dental surveyor of claim 2 including ball bearing means to facilitate the rotation of said spindle within said sleeve and ball bushing means to facilitate the horizontal sliding of said tool housings upon said pairs of parallel horizontal bars.

7. A dental surveyor comprising
   (a) a base;
   (b) a support frame mounted upon said base;
   (c) a vertical sleeve carried by said frame;
   (d) a spindle rotatably received within said sleeve;
   (e) tool support means attached to said spindle below said sleeve, said tool support means comprising a circular disc oriented perpendicular to said spindle and provided with a plurality of slots extending from the perimeter of said disc to the interior thereof; and
   (f) a plurality of tool housings, each carrying a vertical tool and being mounted upon said disc for horizontal sliding within one of said slots along a straight path radial with respect to the axis of rotation of said spindle.

* * * * *